United States Patent [19]
Ouchi

[11] Patent Number: 5,993,474
[45] Date of Patent: Nov. 30, 1999

[54] TREATMENT ACCESSORY FOR ENDOSCOPE

[75] Inventor: Teruo Ouchi, Tokyo, Japan

[73] Assignee: Asahi Kogaku Kogyo Kabushiki Kaisha, Tokyo, Japan

[21] Appl. No.: 08/872,169

[22] Filed: Jun. 10, 1997

[30] Foreign Application Priority Data

| Jun. 11, 1996 | [JP] | Japan | 8-148950 |
| Jun. 21, 1996 | [JP] | Japan | 8-161217 |
| Jun. 24, 1996 | [JP] | Japan | 8-162793 |
| Jun. 24, 1996 | [JP] | Japan | 8-162794 |

[51] Int. Cl.$^6$ .................................................. A61B 17/28
[52] U.S. Cl. ............................ 606/206; 606/113; 606/127
[58] Field of Search ................................ 606/1, 106, 110, 606/113, 167, 128, 151, 108

[56] References Cited

U.S. PATENT DOCUMENTS

| 3,958,576 | 5/1976 | Komiya . |
| 4,178,810 | 12/1979 | Takahashi . |
| 4,467,802 | 8/1984 | Maslanka . |
| 4,655,219 | 4/1987 | Petruzzi . |
| 4,691,705 | 9/1987 | Okada . |
| 4,718,419 | 1/1988 | Okada . |
| 5,258,005 | 11/1993 | Christian . |

FOREIGN PATENT DOCUMENTS 2-39445  10/1990  Japan .

OTHER PUBLICATIONS

"Gastrointestinal Endoscopy", Martin B. Grossman, M.D., *Clinical Symposia*, vol. 32, No. 3, CIBA Pharmaceutical Company, Summit, New Jersey, 1980.

*Primary Examiner*—Glenn K. Dawson
*Attorney, Agent, or Firm*—Greenblum & Bernstein, P.L.C.

[57] ABSTRACT

A treatment unit for an endoscope, for example, a grasping unit is connected at a distal end of a manipulation wire that is connected to a first manipulation member. An inner tube slidably surrounds the manipulation wire. A proximal end of the inner tube is connected to a distal end of a second manipulation member. Further, an outer tube is provided to surround the inner tube and the manipulation wire. A proximal end of the outer tube is connected to a main body connected to the first manipulation a member by a connecting rod that the positional relationship between the manipulation wire and the outer tube along the axis is fixed. By moving the first and second manipulation members towards each other, the grasping unit is opened as the inner tube slides to uncover a part of the grasping unit which opens by resilience, while when the first and second manipulation members are spaced from each other, the inner tube slides to cover a part of the grasping unit forcing it closed.

15 Claims, 15 Drawing Sheets

TREATMENT ACCESSORY FOR ENDOSCOPE

BACKGROUND OF THE INVENTION

The present invention relates to a treatment accessory for an endoscope, especially to a treatment accessory which is used to excise and/or collect material from inside a human body, such as a polyp or the like.

As the treatment accessory of the above type, a grasping accessory is well known. The grasping accessory is provided with a cover tube, an operation wire slidably inserted through the cover tube, and a grasping unit (i.e., grasping forceps) connected at a distal end of the operation wire. The grasping unit is formed of, for example, a pair of wire members having predetermined resilience. The pair of wires neutrally open, and when the wire is pulled with respect to the cover tube so that a portion of the grasping unit is drawn inside the cover tube, the pair of wire members are closed as pushed by the end portion of the cover tube.

When material inside a human body is collected, the grasping accessory is inserted in an instrument channel of the endoscope, and the distal end portion of the grasping accessory is extended from a distal end of the insertion tube of the endoscope, which is inserted in the human body. The grasping unit is further extended from the distal end of the cover tube so that the pair of grasping members open. The grasping unit is then located at a position at which material, such as human tissue or the like is collected, and the operation wire is drawn inside the cover tube in order to close the grasping unit. In this situation, since the grasping unit is to be moved before the pair of grasping wire members are closed, the material may not be collected as intended, or collection may fail.

In order to overcome the above problem, Japanese Utility Model Publication No. HEI-2-39445 proposes a grasping accessory having a double tube structure. In the publication, a manipulation wire is enclosed by an flexible inner tube which is then enclosed by a coaxial flexible outer tube. The grasping accessory also includes a manipulation unit and an openable and closable grasping unit as described above. The grasping accessory operates such that the outer tube is fixed in position with respect to the instrument channel by a clamp member, or the like. The operation of the manipulation unit causes the inner tube to move and close the grasping unit while the grasping unit remains in a fixed position with respect to the axial direction.

However, in the material collecting accessory disclosed in the Japanese Utility Model Publication No. HEI-2-39445 the manipulation unit is designed such that the operation to close the instrument is performed by an operator opening a hand (i.e., separating the thumb and fingers). With such an arrangement, it is difficult to apply sufficient force and is difficult to perform fine or urgent manipulation since the opening/closing movement of the hand is opposite to the opening/closing movement of the instrument.

Further, since the inner and outer tubes and the manipulation wire are all coaxial and connected to the manipulation unit, it is difficult to wash and disinfect the material collecting accessory.

SUMMARY OF THE INVENTION

It is therefore an object of the present invention to provide an improved treatment accessory with which a grasping unit can be manipulated easily.

Another object of the invention is to provide an improved treatment accessory which can be washed and disinfected relatively easily.

According to one aspect of the invention, a treatment accessory for an endoscope comprises an instrument unit having an open state and a closed state, the instrument unit being neutrally in the open state by a resilient force thereof. A first manipulation part is provided, and a second manipulation part is movable in relation to the first manipulation part. A flexible outer tube includes a proximal end where is connected to the second manipulation part. A flexible outer tube is inserted in an instrument channel of the endoscope when in use A, a proximal end of a manipulation wire is fixed in position with respect to the outer tube, a distal end of the manipulation being connected to the instrument unit. A flexible inner tube is slidably inserted in the flexible outer tube, the flexible inner tube slidably surrounding the manipulation wire. A proximal end of the flexible inner tube is connected to the first manipulation part, wherein, when the first manipulation part is located at a position closest to the second manipulation part, the flexible inner tube surrounds the portion of the instrument unit adjacent to the distal end of the manipulation wire to close the instrument unit, and when the first manipulation part is located at a position farthest from the second manipulation part, the flexible inner tube does not cover the portion of the instrument unit adjacent to the distal end of the manipulation wire and the instrument unit is open by resilience.

optionally, the first manipulation part may be provided with a first finger support, the second manipulation part may be provided with a second finger support such that the first manipulation part moves towards the second manipulation part when the first finger support is moved towards the second finger support.

Further optionally, the instrument unit may include a grasping collecting unit.

Further optionally, the instrument unit may be basket-type collecting unit, the basket-type collecting unit comprising a plurality of flexible wires connected at both ends.

Alternatively, the instrument unit may be a snare unit, the snare unit comprising at least one flexible wire formed into a loop. In this case, the snare unit may be a highfrequency snare unit.

According to another aspect of the invention, a treatment accessory for an endoscope comprises a treatment unit end; an inner tube. An outer tube is coaxially provided around the inner tube and, a manipulation wire is slidably inserted in the inner tube. A distal end of the manipulation wire is attached to the treatment unit, and a first manipulation part is connected to a proximal end of the manipulation wire. A second manipulation part is connected to a proximal end of the inner tube, and a main body is connected to a proximal end of the outer tube. A connecting member connects the first manipulation part and the main body, the connecting member being displaced from and parallel to an axis of the manipulating wire, wherein the second manipulation part is slidable along the connecting member.

With the treatment accessory according to this aspect, since the first manipulation part and the second manipulation part are connected by the connecting member that is not coaxial with the manipulation wire, the manipulation wire and the first and second manipulation parts can be quickly and easily washed after each use.

Optionally, the connecting member may be detachable from one of the first manipulation part and the second manipulation part. Further optionally, the manipulation wire may be detachable from the first manipulation part. In this way, the manipulation wire, inner tube, and outer tube can be easily disassembled and washed and disinfected individually.

Still further, the treatment instrument may be formed to resiliently open.

Furthermore, the treatment instrument is closed when the inner tube slides to cover a portion of the treatment unit adjacent to the distal end of the manipulation wire.

Optionally, the instrument unit includes a grasping collecting unit.

Alternatively, the instrument unit may include a basket-type collecting unit and the basket-type collecting unit may include a plurality of flexible wires connected at both ends.

Further alternatively, the instrument unit may be a snare unit including at least one flexible wire formed into a loop. In this case, the snare unit may be a high-frequency snare unit.

According to a further aspect of the invention, a basket accessory for endoscope includes: a basket-type collecting unit having a plurality of flexible wires connected at both ends, a first manipulation part and second manipulation. The first manipulation part is movable in relation to the second manipulation part. A proximal end of a flexible outer tube is connected to the second manipulation part, the flexible outer tube being inserted in an instrument channel of the endoscope when in use. A proximal end of a manipulation wire is fixed in position with respect to the outer tube, a distal end of the manipulation wire being connected to the basket-type collecting unit. A flexible inner tube is slidably inserted in the flexible outer tube, the flexible inner tube slidably surrounding the manipulation A proximal end of the flexible inner tube is connected to the first manipulation part, wherein the basket-type collecting unit is neutrally open due to resilience, and wherein, when a distal end portion the flexible inner tube is slides to cover a portion of the basket-type collecting unit adjacent to the distal end of the manipulation wire, the basket-type collecting unit is closed.

According to a still further aspect of the invention, a snare accessory for an endoscope includes a snare unit having a plurality of flexible wires connected at both ends, a first manipulation part, and second manipulation part. The first manipulation part is movable in relation to the second manipulation part. A proximal end of a flexible outer tube is connected to the second manipulation part, the flexible outer tube being inserted in an instrument channel of the endoscope when in use. A proximal end of a manipulation wire is fixed in position with respect to the outer tube, a distal end of the manipulation wire being connected to the snare unit flexible inner tube is slidably inserted in the flexible outer tube, the flexible inner tube slidably surrounding the manipulation wire. A proximal end of the flexible inner tube is connected to the first manipulation part, wherein the snare unit is neutrally open due to resilience, and wherein, when a distal end portion of the flexible inner tube slides to cover a portion of the snare unit adjacent to the distal end of the manipulation wire, the snare unit is closed.

DETAILED DESCRIPTION OF THE PREFERRED EMBODIMENTS

Embodiments of the present invention are described with reference to the figures.

Figure 1:
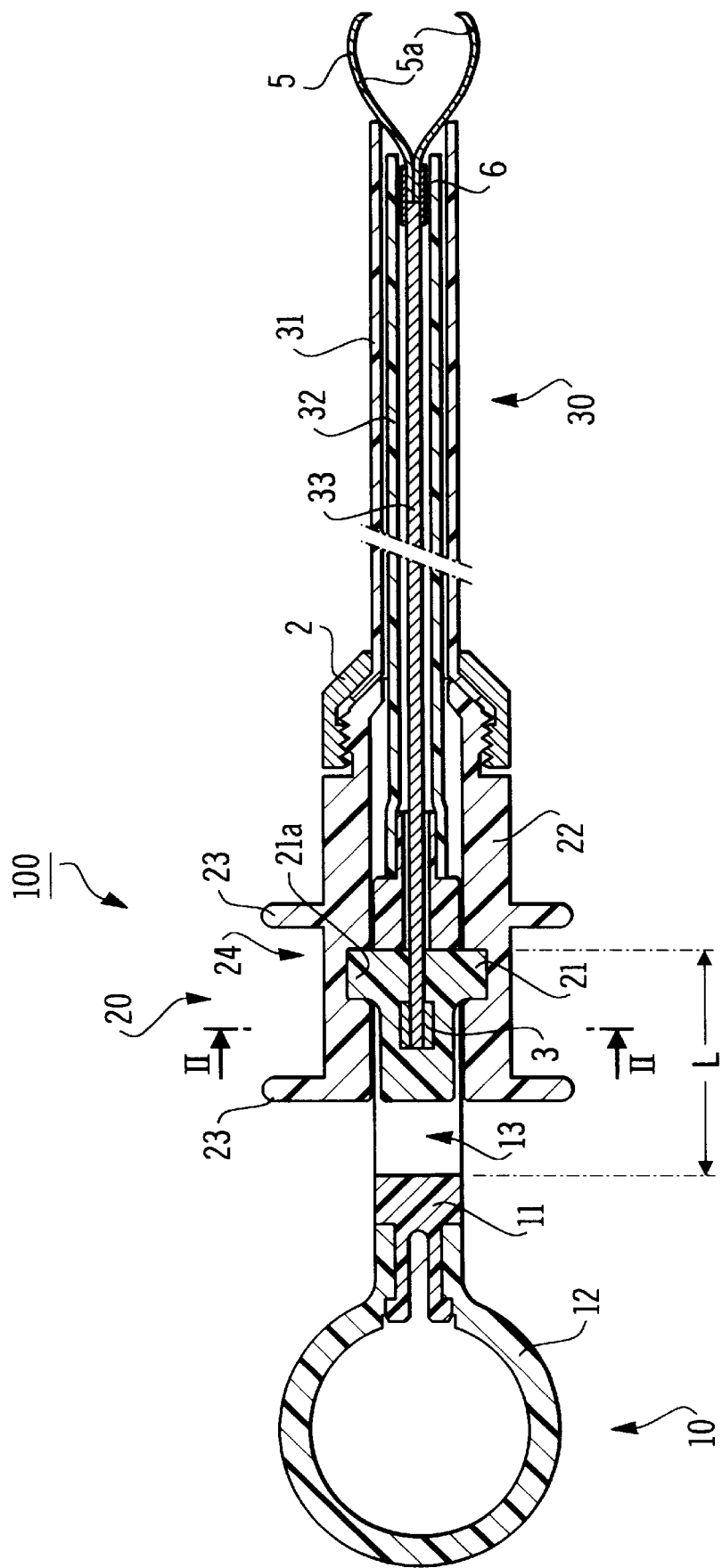
FIG. 1 is a sectional side view of a material collecting accessory according to an embodiment of the invention.
Figure 2:
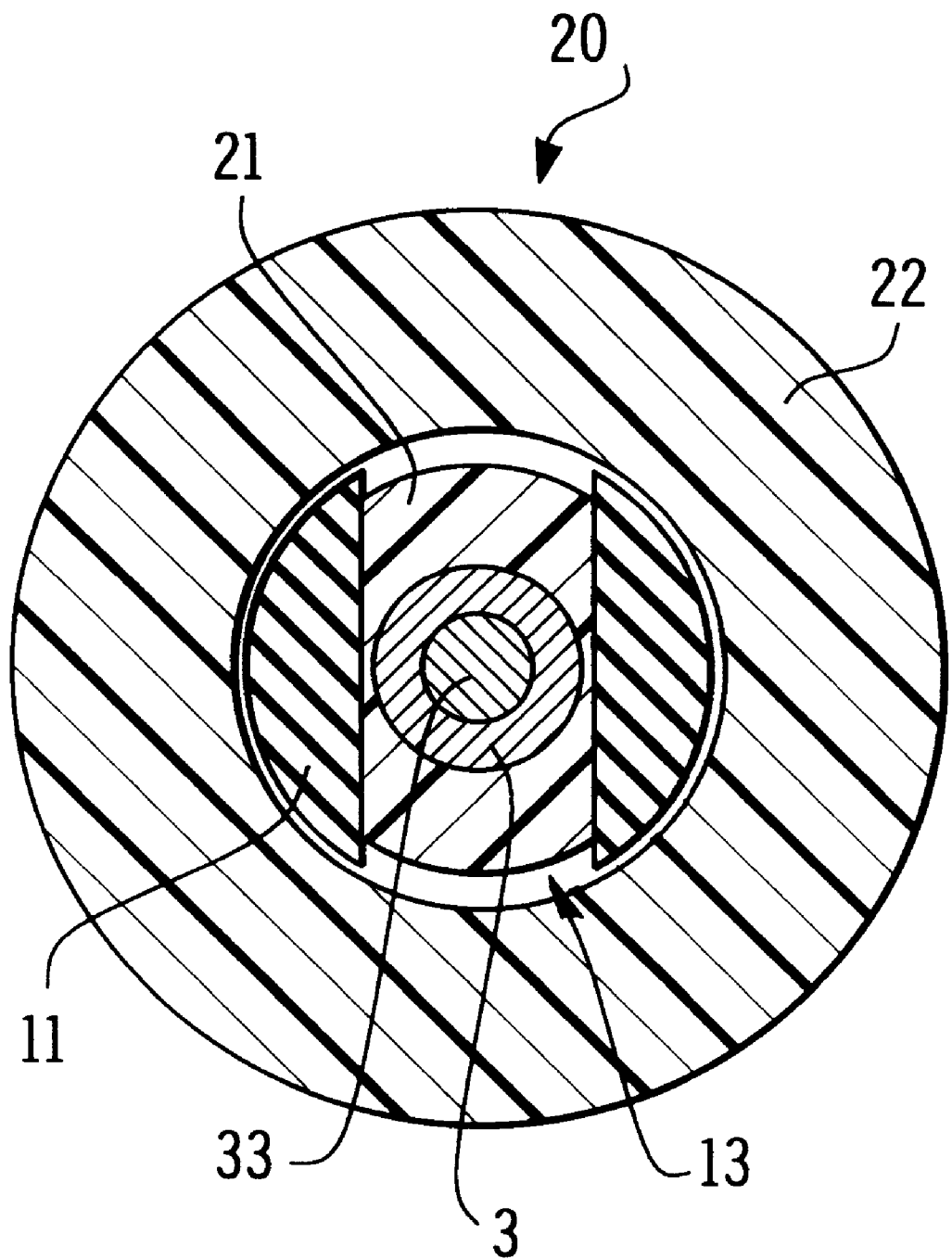
FIG. 2 is an enlarged cross section taken on line II—II of FIG. 1.

FIG. 1 is a sectional view of a material collecting accessory (i.e., a treatment instrument) 100 according to an embodiment of the invention. FIG. 2 is a cross section taken along the line II—II in FIG. 1. Referring to FIGS. 1 and 2, the material collecting accessory 100 includes a first manipulation part 10, a second manipulation part 20, and an insertion part 30.

Figure 4:
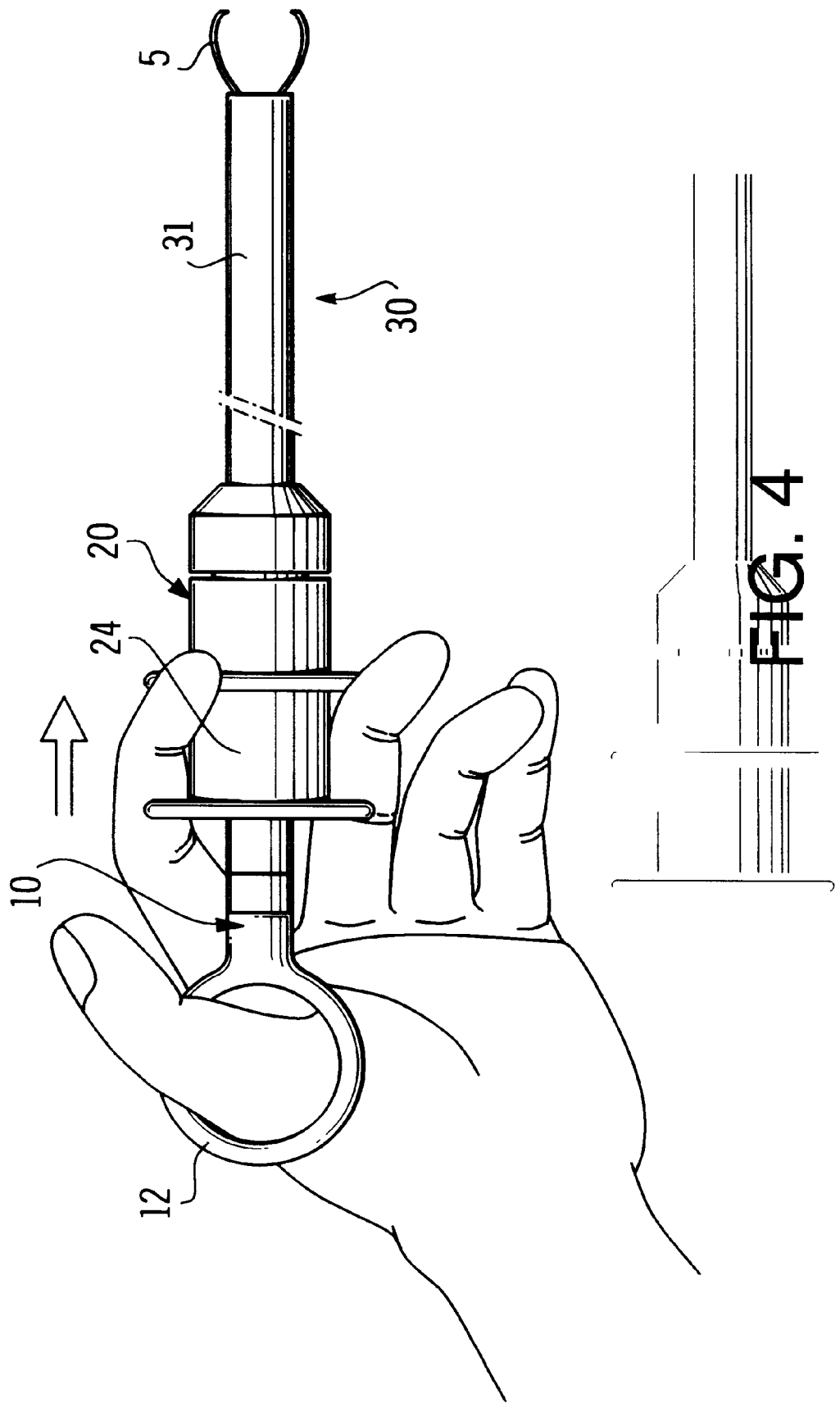
FIG. 4 is a side view illustrating the operation of the material collecting accessory of FIG. 1.
Figure 5:
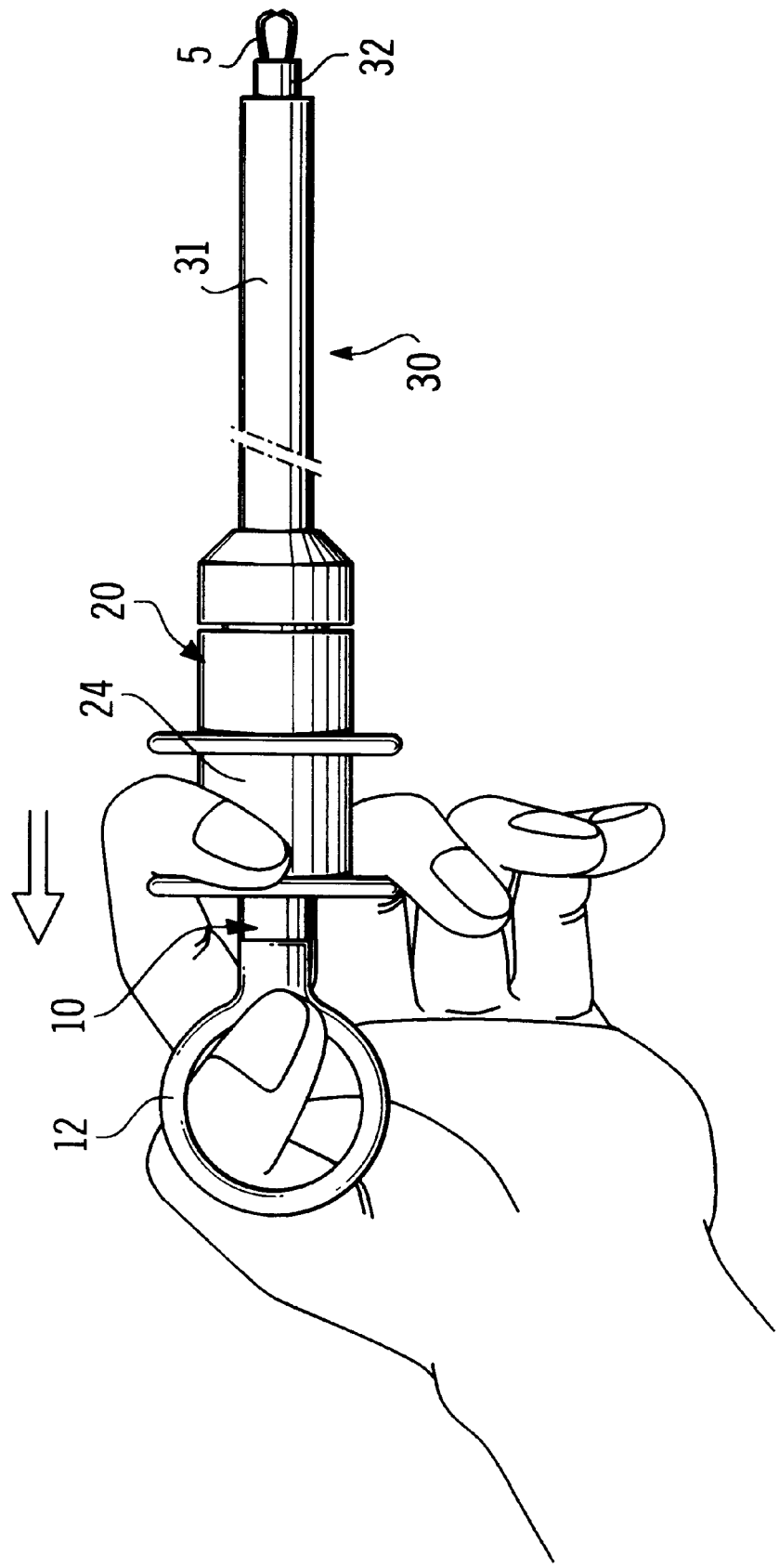
FIG. 5 is a side view illustrating the operation of the material collecting accessory of FIG. 1 in a closed state.

The first manipulation part 10 includes a support 12 and a cylindrical shaft 11. The support 12 is, e.g., a first grasping portion held by an operator to operate the accessory, as shown in FIGS. 4 and 5. The support 12 is attached to a proximal side of the shaft 11. The shaft 11 is provided with a narrow central slit 13 formed for a predetermined length L along an axial direction of the shaft 11. The distal end of the shaft 11 is attached to an inner tube 32 (described below).

The second manipulation part 20 includes a slide piece 21 and a cylindrical slider barrel 22. The slide piece 21 is disposed to the shaft 11 inside the slit 13 in a manner enabling axial movement along the predetermined length L of the slit 13 and is connected to the slider barrel 22 by an extending part 21a that extends from the slide piece 21 and protrudes from the slit 13 to contact the slider barrel 22. Thus, the first manipulation part 10 and the second manipulation part 20 are arranged to slide with respect to each other in the axial direction.

An outer peripheral surface of the slider barrel 22 is provided with gripping flanges 23 which define a grasping area 24 that is held by an operator during operation of the material collecting accessory 100. The grasping area 24 is, e.g., a second grasping portion held by an operator the accessory, as shown in FIGS. 4 and 5.

The insertion part 30, which is passed through an instrument insertion channel of an endoscope (not shown), includes an outer tube 31, an inner tube 32, and a manipulation wire 33. The outer tube 31 and the inner tube 32 are formed, for example, from a flexible material, such as tetrafluoroethylene or the like. A proximal end of the outer tube 31 is connected to the slide barrel 22 by a fixing nut 2 which is screwed onto a distal end of the slide barrel 22.

The inner tube 32 has an outer diameter that is smaller than the inner diameter of the outer tube 31 and is disposed coaxially inside the outer tube 31 such that the inner tube 32 may move relative to the outer tube 31 in the axial direction. A proximal end of the inner tube 32 is connected to a distal end of the shaft 11.

The flexible manipulation wire 33 is provided coaxially inside the inner tube 32, such that the manipulation wire 33 may move in the axial direction relative to the inner tube 32. As shown in FIG. 2, a fixed block 3 provided at a proximal end of the manipulation wire 33, formed, for example, by brazing, is embedded in the slide piece 21.

The distal end of the manipulation wire 33 is provided with a connecting tube 6 that connects the manipulation wire 33 to a grasping unit 5. The grasping unit 5 is formed from two wires 5a made of a resilient material, such as stainless steel, such that, in a neutral state (i.e., when no external forces are applied), the grasping unit 5 tends to open due to resilience, as shown in FIG. 1.

With the above arrangement, the second manipulation part 20 is attached to both the outer tube 31 and the manipulation wire 33 such that the outer tube 31 and the manipulation wire 33 do not move relative to each other, while the first manipulation part 10 is attached to the inner tube 32 such that movement of the first manipulation part 10 in relation to the second manipulation part 20 moves the inner tube 32 in the axial direction in relation to both the outer tube 31 and the manipulation wire 33.

Figure 3:
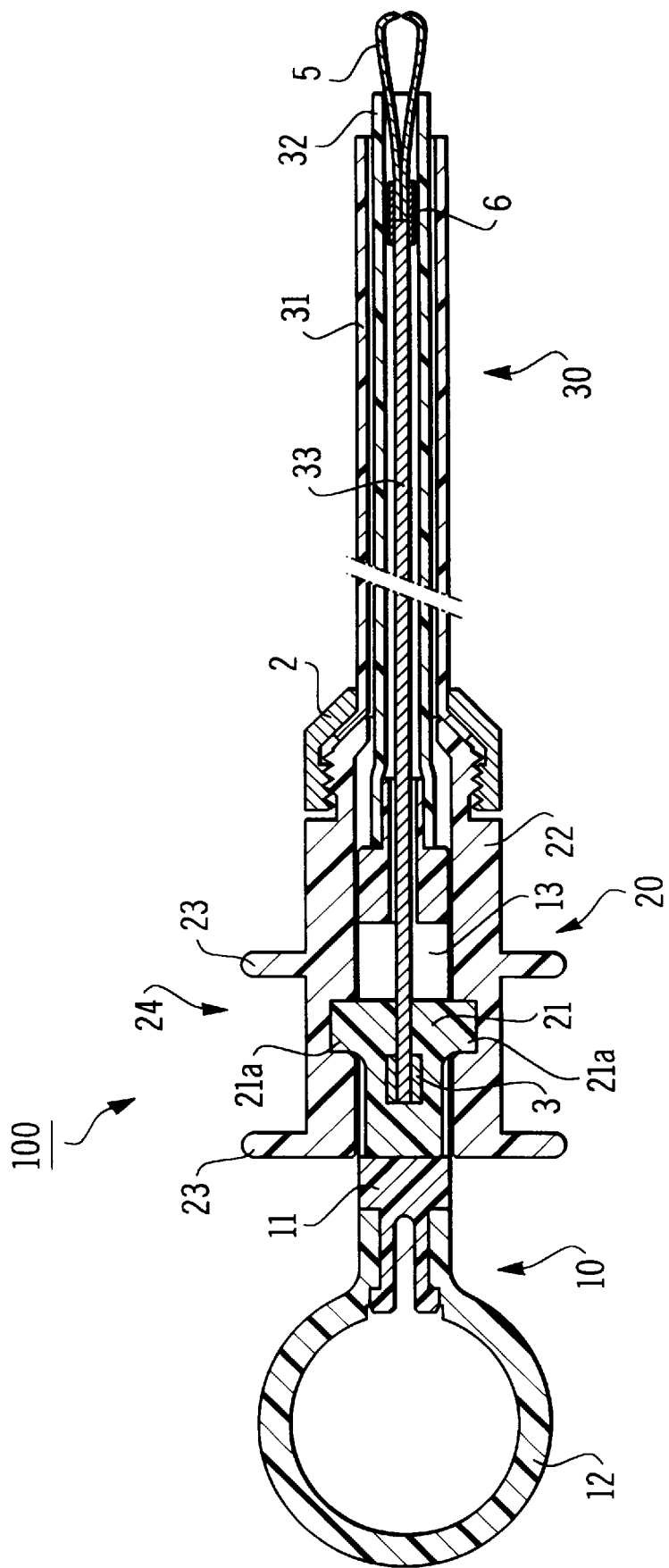
FIG. 3 is a sectional side view of the material collecting accessory of FIG. 1 in a closed state.

In particular, when the second manipulation part 20 is at a distal position with respect to the first manipulation part 10, a distal end of the inner tube 32 is positioned slightly inside the distal end of the outer tube 31, as shown in FIG. 1. When, as shown in FIG. 3, the second manipulation part 20 is set at a proximal position with respect to the first manipulation part 10, the distal end of the inner tube 32 protrudes from the distal end of the outer tube 31.

The operation of the material collecting accessory 100 is now described with reference to FIGS. 4 and 5. FIGS. 4 and 5 illustrate states in which an operator has, respectively, opened and closed the grasping unit 5 by operation of the first manipulation part 10 and the second manipulation part 20. In this example, the operator engages a thumb with the support 12 and two fingers with the grasping area 24, although other arrangements are also possible.

As shown in FIG. 5, when the grasping area 24 is closer to the support 12 (i.e., a closed hand), the distal end of the inner tube 32 protrudes from the distal end of the outer tube 31 and the grasping unit 5 is closed. Also, as shown in FIG. 4, when the grasping area 24 is further from the support 12 (i.e., an open hand), the distal end of the inner tube 32 is inside the distal end of the outer tube 31 allowing the grasping unit 5 to open resiliently.

Thus, when inserting the material collecting accessory 100 through an instrument insertion channel of an endoscope (not shown) the operator's hand is closed as shown in FIG. 5 so that the insertion part 30 passes through the instrument insertion channel with the grasping unit 5 closed.

Once inside a human body (not shown), the grasping unit 5 is opened by opening the hand (as shown in FIG. 4) and the outer tube 31 is positioned so that the material is positioned within the opened grasping unit 5. At this point, the outer tube 31 is fixed in position by a forceps plug, clamp, or the like (not shown) provided at a proximal end of the endoscope so that an operator can then accurately operate the first and second manipulation parts 10, 20. The operator then closes the hand to slide the inner tube 32 over the grasping unit 5 and close the grasping unit 5 as shown in FIG. 5. In this operation, since the outer tube 31 is fixed in the axial direction, the grasping unit 5 remains fixed in the axial direction while being closed by the sliding of the inner tube 32, and thus, the material can be grasped securely and removed from the human body by drawing out either the material collecting accessory or the endoscope.

Figure 6:
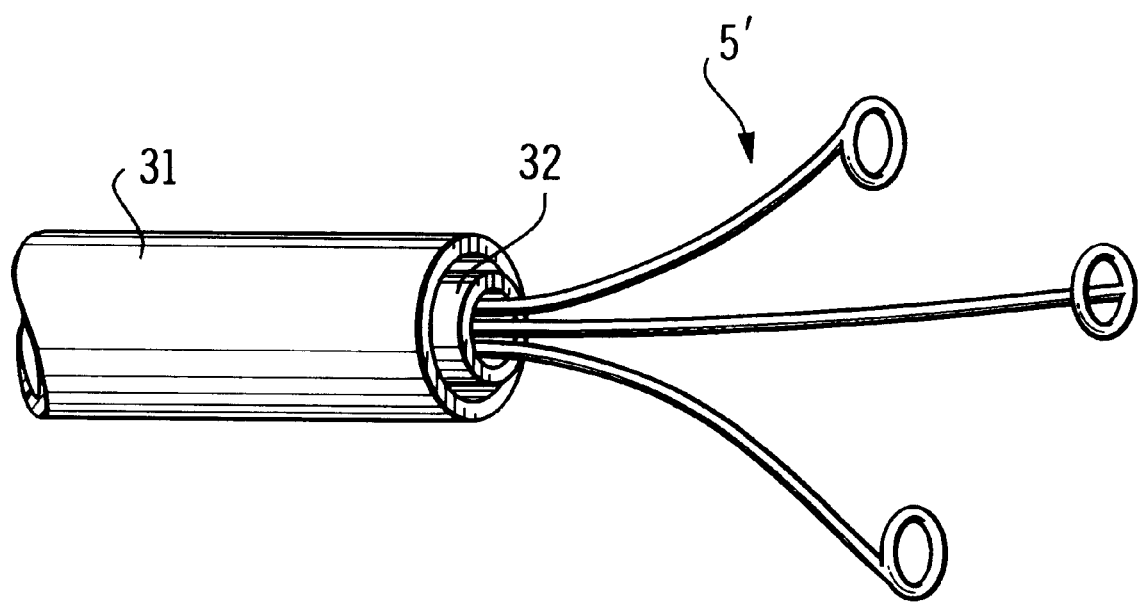
FIG. 6 is a perspective view of an alternative grasping unit for the material collecting accessory of FIG. 1.
Figure 7:
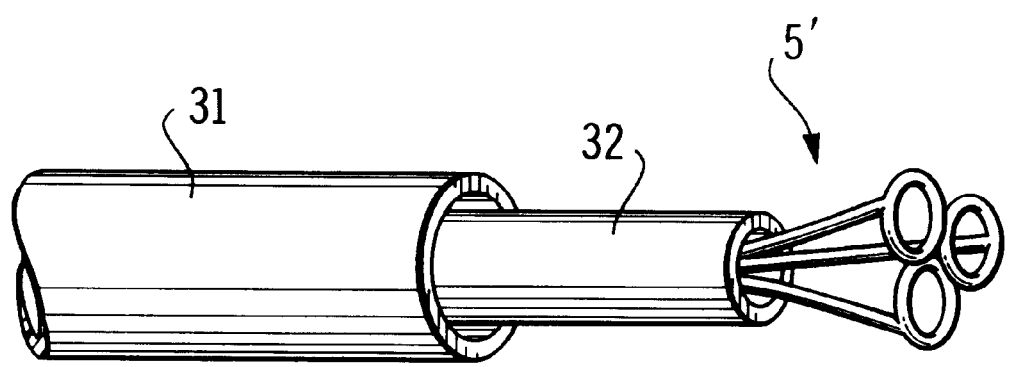
FIG. 7 is a perspective view of the alternative grasping unit of FIG. 6 in a closed state.

The grasping unit 5 is not limited to the arrangement described above. For example, an alternative grasping unit 5' is shown in FIGS. 6 and 7. The grasping unit 5' is formed from three resilient wires and is shown in an opened state in FIG. 6 and in a closed state in FIG. 7.

With the material collecting accessory 100, since the grasping unit 5 does not move in the axial direction during closing, the material can be securely grasped. Further, since the operations of closing and opening the grasping unit 5 are performed by corresponding movements of the operator's hand, that is, by closing and opening the hand, respectively, the operator may apply a stronger force to close the grasping unit 5 and more accurately control the operation of the grasping unit 5.

A material collecting accessory 200 according to another embodiment of the invention is now described with reference to FIGS. 8 to 12. In this embodiment, the insertion part 30 and the grasping unit 5 are substantially identical to those of the previous embodiment and identical reference numbers are used. The material collecting accessory 200 of this embodiment provides the benefit of maintaining the axial position of the grasping device 5 during closing while also being easy to clean and disinfect.

Figure 8:
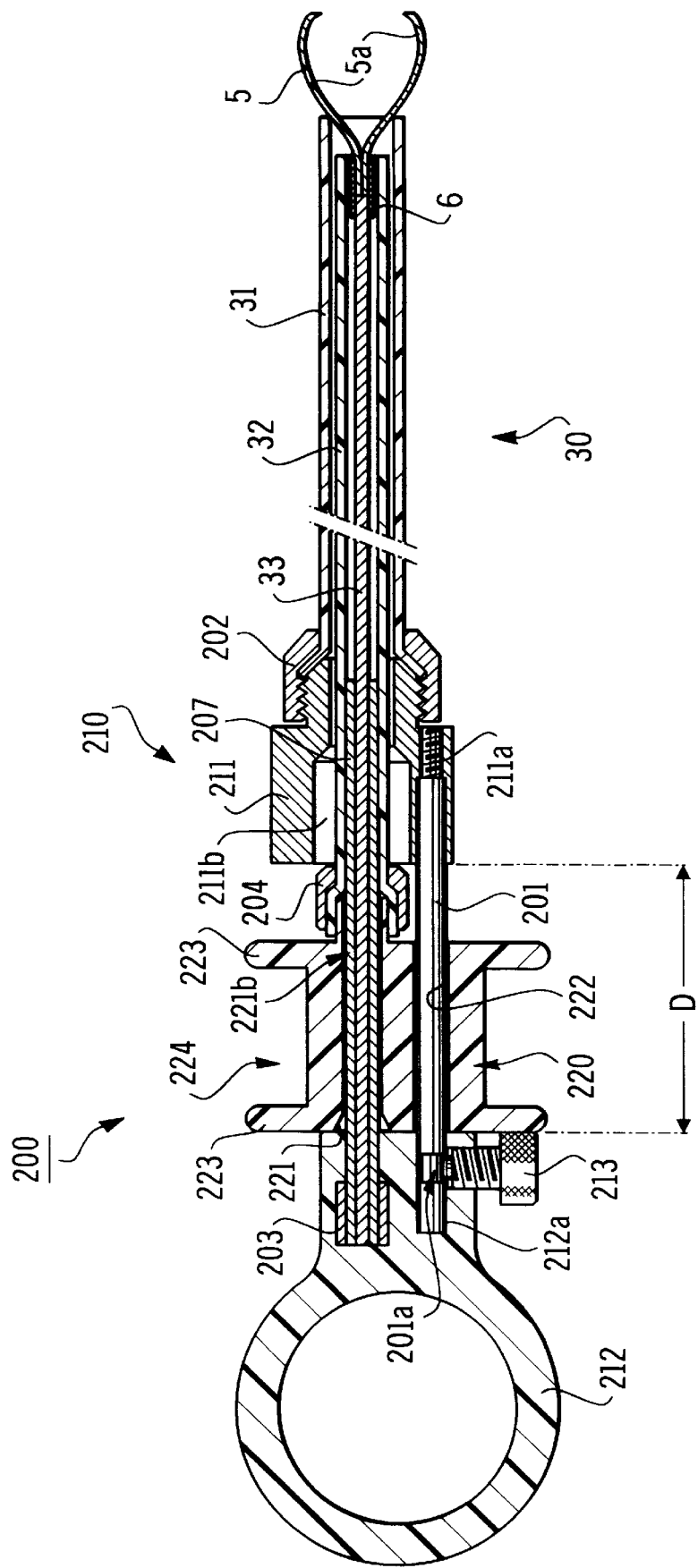
FIG. 8 is a sectional side view of a material collecting accessory according to another embodiment of the invention.

FIG. 8 is a sectional view of the material collecting accessory 200. The material collecting accessory 200 includes a first manipulation part 210, a second manipulation part 220, and the insertion part 30.

The first manipulation part 210 includes a support 212 and a cylindrical body 211. The support 212 is connected to the body 211 at a predetermined distance D from a proximal side of the body 211 by a connecting rod 201 that is parallel to the axis of the insertion part 30.

The distal end of the connecting rod 201 is attached to the body 211 by, for example, a screw thread 211a. Further, the proximal end of the connecting rod 201 fits into a hole 212a formed on the support 212 and is fixed to the support 212 by a fixing screw 213 that is screwed into the support 212 perpendicular to the connecting rod 201. In order to ensure that the predetermined distance D is maintained between the body 211 and the support 213 even if the fixing screw 213 becomes loose, a circumferential groove 201a is formed on the connecting rod 201 into which the tip of the fixing screw 213 may be inserted.

Thus, the support 212 is fixed to the body 211 but can be disengaged by loosening the fixing screw 213 for cleaning.

Further, if necessary, it is also possible to unscrew the connecting rod 201 from the body 211.

The body 211 is further provided with an axial through hole 211b through which the inner tube 32 passes. The proximal end of the outer tube 31 is fixed over the axial through hole 211b at the distal end of the body 211 by a fixing nut 202 that is, for example, screwed onto the distal end of the body 211.

The second manipulation part 220 is provided in the space between the body 211 and the support 212. The proximal end of the inner tube 32 extends through the axial through hole 211b and is connected to the second manipulation part 220 by a holding tube 204.

The second manipulation part 220 is provided with through holes 221 and 222 through which the manipulation wire 33 and the connecting rod 201 pass, respectively. In particular, the manipulation wire 33 passes loosely through the through hole 221 and the connecting rod 201 passes slidably through the through hole 222. Thus, the second manipulation part 220 may slide axially along the connecting rod 201 within the predetermined distance D between the body 211 and the support 212.

An outer peripheral surface of the second manipulation part 220 is provided with gripping flanges 223 which define a grasping area 224 that is held by an operator during operation of the material collecting accessory 200.

The manipulation wire 33 passes through the through hole 221 between the body 211 and the support 212 and is provided with a fixing block 203 that is embedded in the support 212. Also, as shown in FIG. 8, the manipulation wire 33 is further provided with a rigid member 207, such as a stainless steel pipe or the like, that covers the manipulation wire 33 from the support 212 to slightly inside the entrance to the inner tube 32 in order to prevent the manipulation wire 33 from buckling during operation of the collecting accessory 200.

Thus, with this arrangement, the first manipulation part 210 is attached to both the outer tube 31 and the manipulation wire 33 such that the outer tube 31 and the manipulation wire 33 do not move relative to each other, while the second manipulation part 220 is attached to the inner tube 32 such that the movement of the second manipulation part 220 in relation to the first manipulation part 210 moves the inner tube 32 in the axial direction in relation to both the outer tube 31 and the manipulation wire 33.

Figure 9:
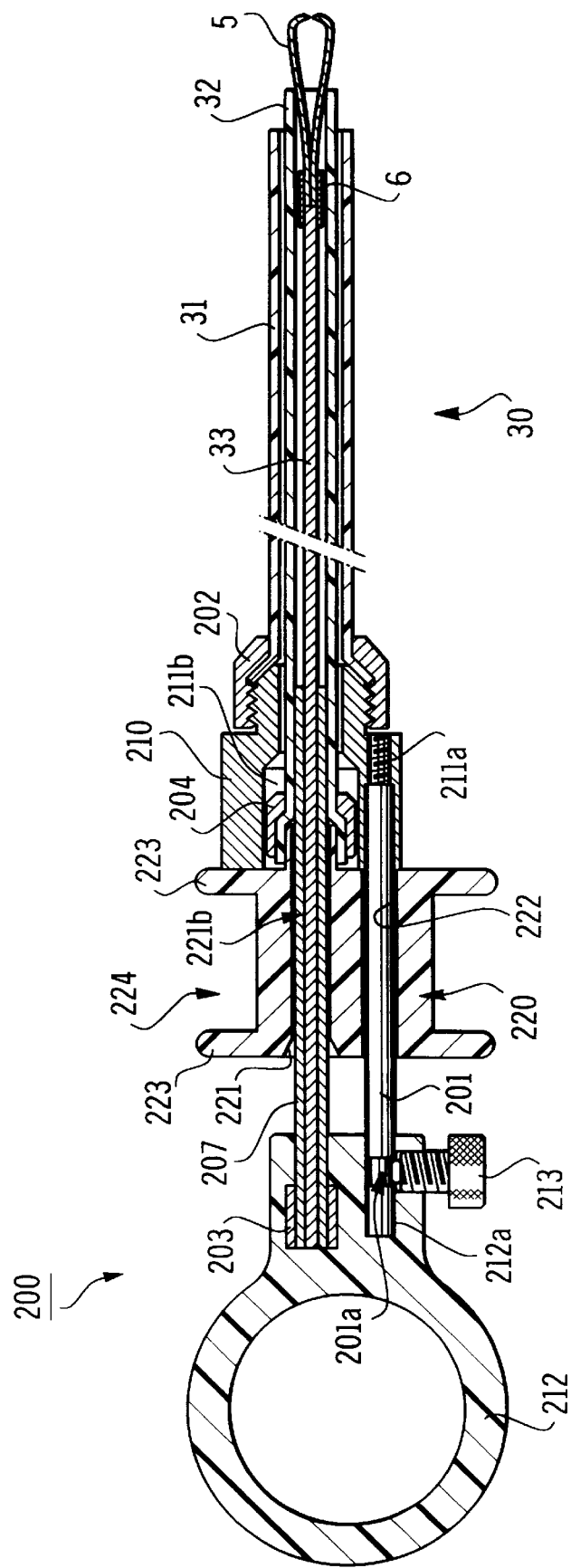
FIG. 9 is a sectional side view of the material collecting accessory of FIG. 8 in a closed state.

In particular, when the second manipulation part 220 is at a proximal position with respect to the first manipulation part 210, a distal end of the inner tube 32 is positioned slightly inside the distal end of the outer tube 31, as shown in FIG. 8. When, as shown in FIG. 9, the second manipulation part 220 is set at a distal position with respect to the first manipulation part 210, the distal end of the inner tube 32 protrudes from the distal end of the outer tube 31.

Figure 10:
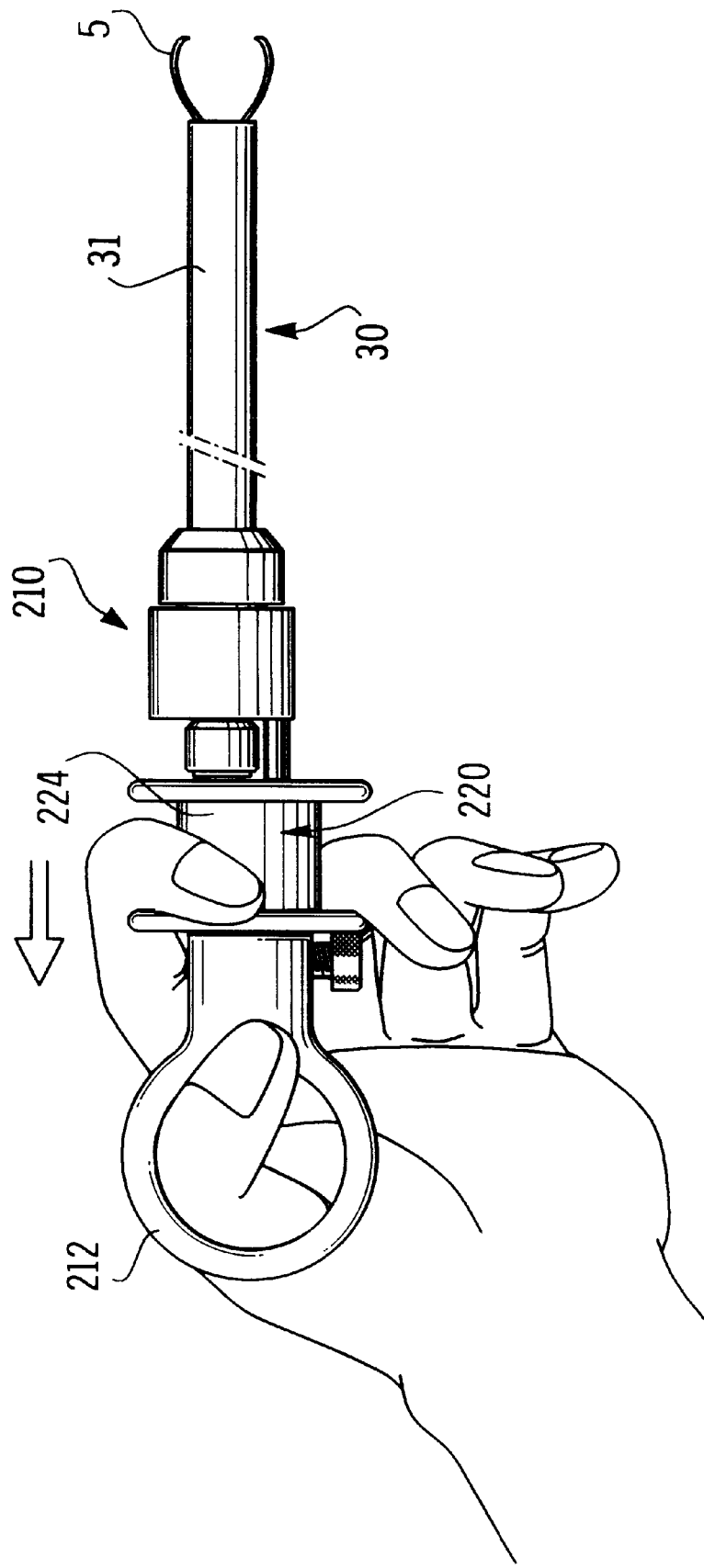
FIG. 10 is a side view illustrating the operation of the material collecting accessory of FIG. 8.
Figure 11:
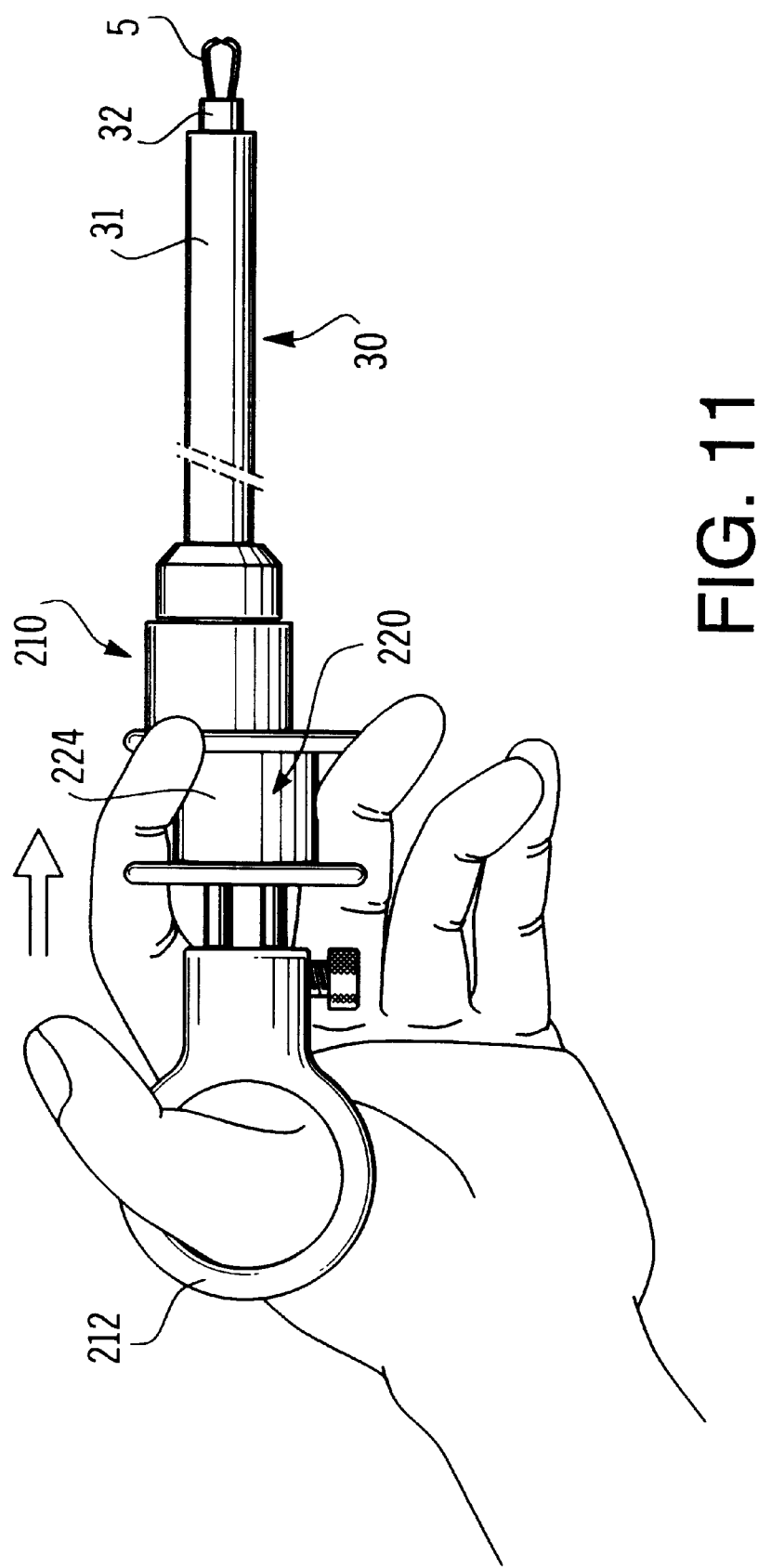
FIG. 11 is a side view illustrating the operation of the material collecting accessory of FIG. 8 in a closed state.

The operation of the material collecting accessory 200 is now described with reference to FIGS. 10 and 11. FIGS. 10 and 11 illustrate states in which an operator has, respectively, opened and closed the grasping unit 5 by operation of the first manipulation part 210 and the second manipulation part 220. In this example, the operator has engaged a thumb with the support 212 and two fingers with the grasping area 224, although other arrangements are also possible.

As shown in FIG. 11, when the grasping area 224 is further from the support 212, the distal end of the inner tube 32 protrudes from the distal end of the outer tube 31 and the grasping unit 5 is closed. Also, as shown in FIG. 10, when the grasping area 24 is closer to the support 12, the distal end of the inner tube 32 is inside the distal end of the outer tube 31 allowing the grasping unit 5 to open resiliently.

Thus, when inserting the material collecting accessory 200 through the instrument insertion channel of an endoscope the grasping unit 5 is held closed as shown in FIG. 11 so that the insertion part 30 passes through the instrument insertion channel easily.

Once inside a human body (not shown), the grasping unit 5 is opened (as shown in FIG. 10) and the outer tube 31 is positioned so that the material is positioned within the opened grasping unit 5. At this point, the outer tube 31 is fixed in position by a forceps plug, clamp, or the like (not shown) provided at a proximal end of the endoscope so that an operator can then accurately operate the first and second manipulation parts 210, 220. The operator then slides the inner tube 32 over the grasping unit 5 and closes the grasping unit 5 as shown in FIG. 11. In this operation, since the outer tube 31 is fixed in the axial direction, the grasping unit 5 remains in a fixed position in the axial direction while being closed by the sliding of the inner tube 32, and thus, the material can be grasped securely.

With the material collecting accessory 200, since the body 211 and the support 212 are connected by a single connecting rod 201 that is disposed parallel to, but at a side of, the manipulation wire 33, washing and disinfecting can be performed easily after each use.

For example, washing solution (not shown) can be injected into the inner tube 32 through the through hole 221. Preferably, a proximal end of the through hole 221 is appropriately tapered for this purpose as shown in FIGS. 8 and 9. Similarly, washing solution can be injected into the outer tube 31 through the body 211 when the second manipulation part 220 is moved to a proximal position with respect to the first manipulation part 210.

Further, by disengaging the connecting rod 201 and the support 212 by loosening the fixing screw 213 and pulling the support 212 towards the proximal side, the manipulation wire 33 can be pulled out towards the proximal side from inside the inner tube 32. The manipulation wire 33 can thereby be washed adequately.

Furthermore, the inner tube 32 can be pulled out of the outer tube 31 by pulling the second manipulation part 220 towards the proximal side with respect to the body 211 to allow the inner tube 32 and the inside of the outer tube 33 to be washed and disinfected.

Figure 12:
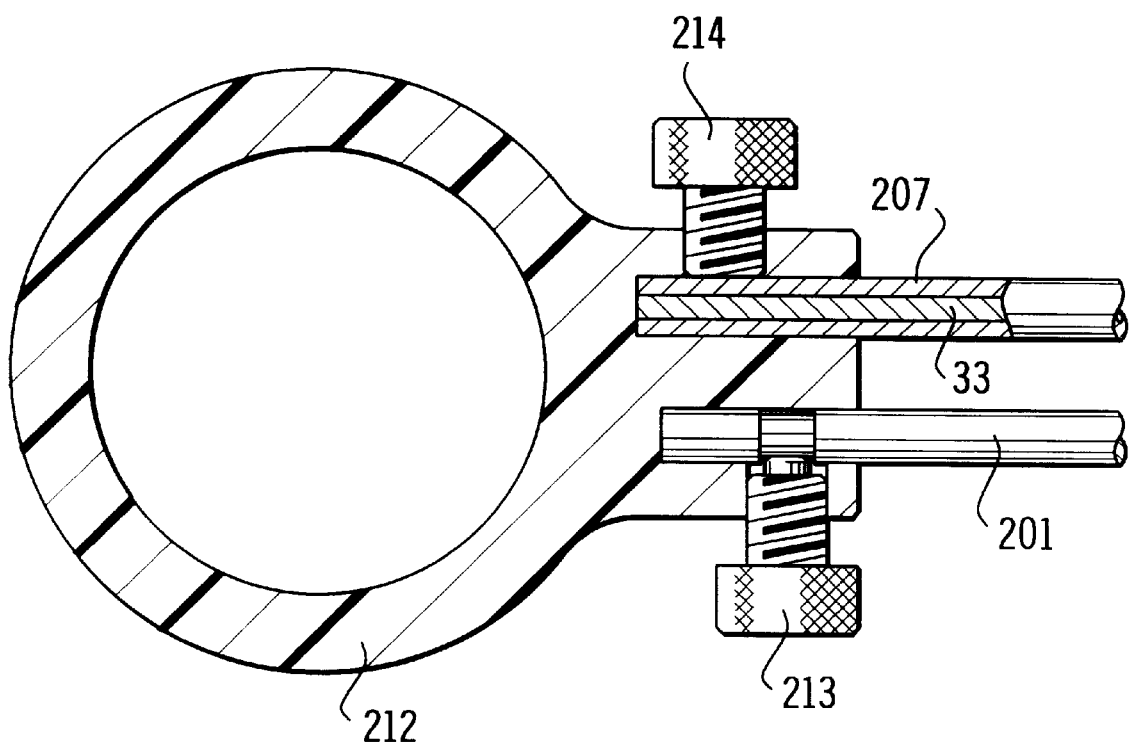
FIG. 12 is an enlarged sectional side view of an alternative grasping unit 5 for the material collecting accessory of FIG. 8.

If the grasping unit 5 is too large to pass through the inner tube 32, the manipulation wire 33 (and the rigid member 207) may be fixed to the support 212 by a second fixing screw 214 as shown in FIG. 12. With such an arrangement, since the connection of the manipulation wire 33 with the support 212 can be disengaged by loosening the fixing screw 214, the manipulation wire 33 can be pulled out of the inner tube 32 by pulling the grasping unit 5 in the distal direction.

As described above with reference to FIGS. 6 and 7, in this embodiment, the grasping unit 5 is also not limited to the shape, arrangement, and the like as described above.

Figure 13:
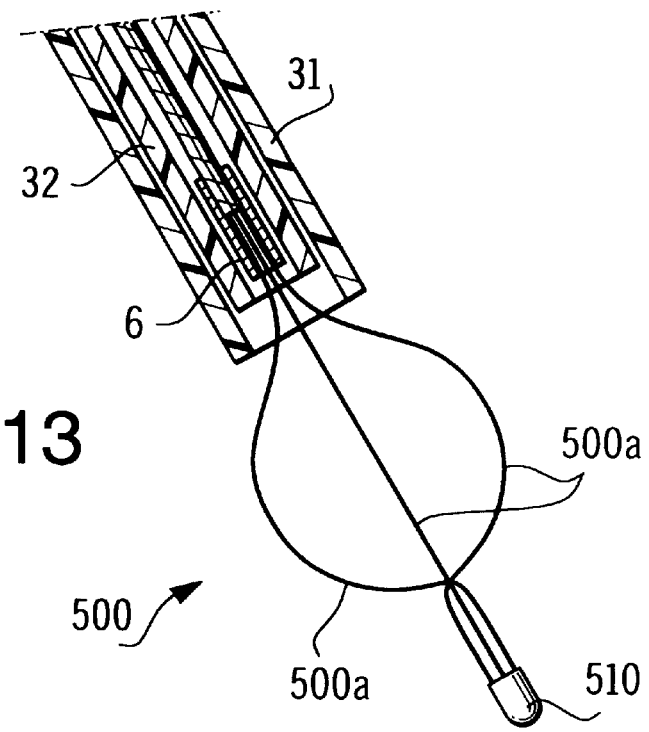
FIG. 13 is an enlarged sectional side view of an alternative material collecting accessory.

Further, the concept of using a double-tube structure according to the embodiments can be applied to other operative instruments as well. For example, as shown in FIG. 13, the grasping unit 5 of the above embodiments may be replaced by a basket-type collecting accessory 500 that is similarly connected to the proximal end of the manipulation wire 33 by the connecting tube 6. The basket-type collecting instrument 500 is formed, for example, from four stranded stainless steel wires 500a that are connected at a distal end by an end tip 510. The wires 500a are resilient and are formed such that in a neutral state the wires 500a have a basket-like form, as shown in FIG. 13.

Figure 14:
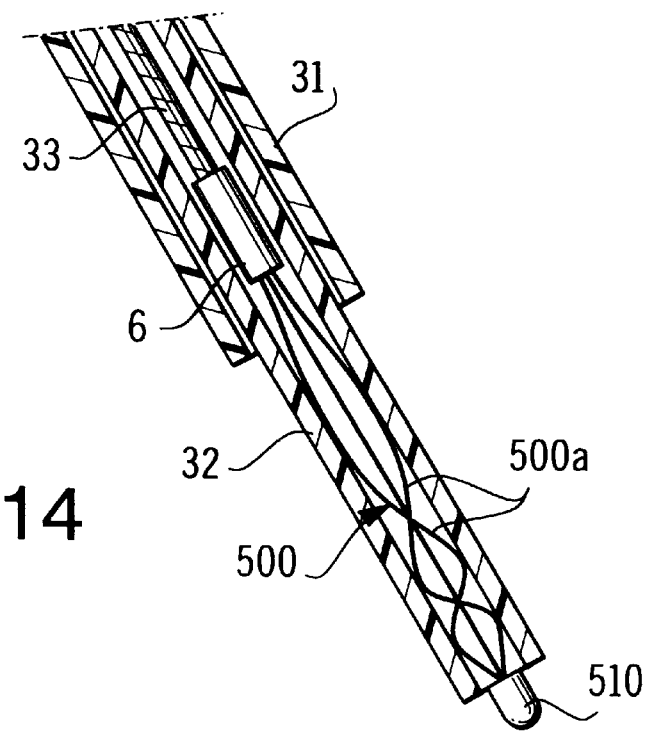
FIG. 14 is an enlarged sectional side view of the alternative material collecting accessory of FIG. 13 in a closed state.

If the basket-type collecting unit 500 is provided to the material collecting accessory 100 of the first embodiment as an example, as shown in FIGS. 5 and 14, when the grasping area 24 is brought closer to the support 12 (that is, by closing the hand), the distal end of the inner tube 32 protrudes from the distal end of the outer tube 31 and closes the basket-type collecting unit 500.

Also, as shown in FIGS. 4 and 13, when the grasping area 24 is moved away from the support 12 (that is, by opening the hand), the distal end of the inner tube 32 moves inside the distal end of the outer tube 31 allowing the basket-type collecting unit 500 to open resiliently.

As is shown in FIG. 14, in this example, the inner tube 32 may need to extend a longer length than in the first embodiment. Thus, in this case, the predetermined length L of the slit 13 may be made longer to accommodate the length of the basket-type collecting unit 500.

When inserting the material collecting accessory 100 through the instrument insertion channel of an endoscope, the basket-type collecting unit 500 is closed.

Figure 15:
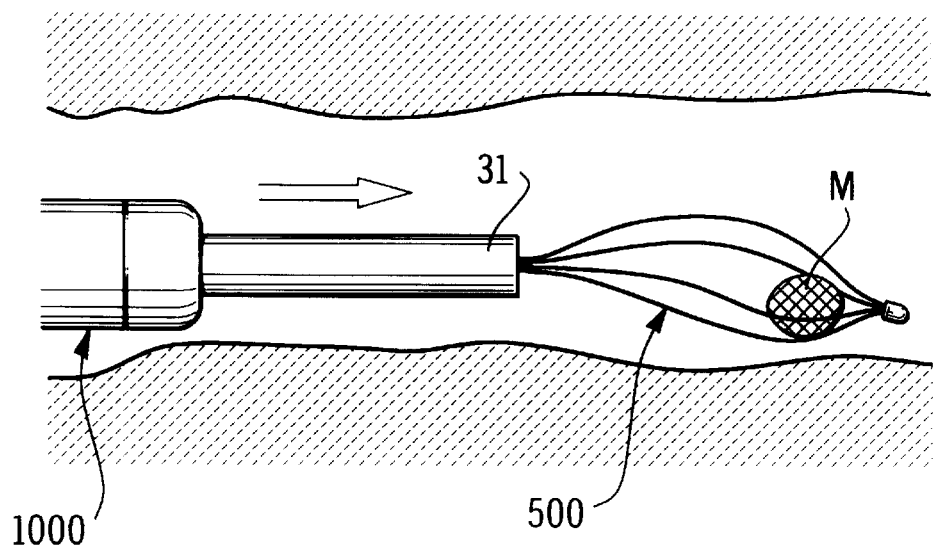
FIG. 15 is a side view illustrating the operation of the material collecting accessory of FIG. 13.
Figure 16:
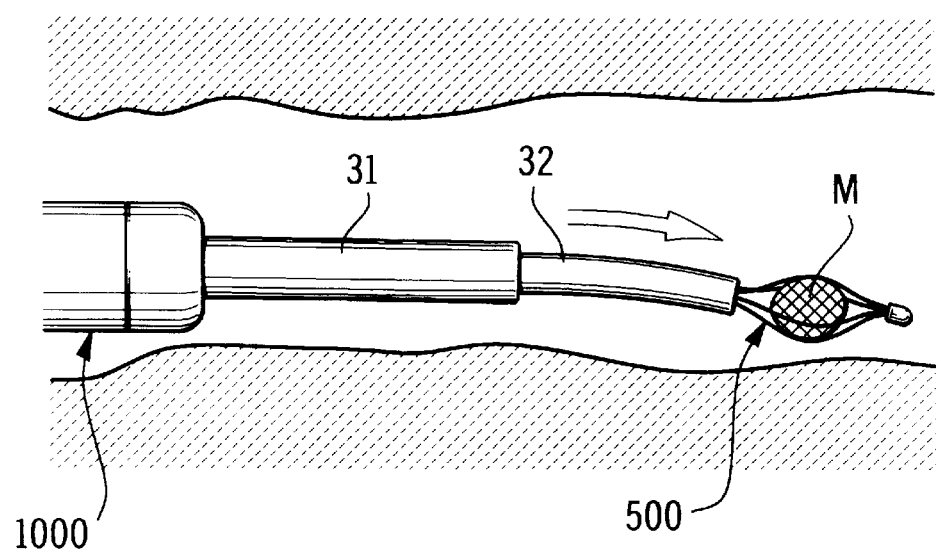
FIG. 16 is a side view illustrating the operation of the material collecting accessory of FIG. 13 in a closed state.

Once inside a human body, the basket-type collecting unit 500 is opened and the outer tube 31 is positioned so that some material M is positioned inside the opened basket-type collecting unit 500 (as shown in FIG. 15). At this point, the outer tube 31 is fixed in position by a forceps plug, clamp, or the like (not shown) provided at a proximal end of the endoscope so that an operator can then accurately operate the first and second manipulation parts 10, 20. The operator then slides the inner tube 32 over the basket-type collecting unit 500 and close the basket-type collecting unit 500 (as shown in FIG. 16). In this operation, since the outer tube 31 is fixed in the axial direction, the basket-type collecting unit 500 remains fixed in the axial direction while being closed by the sliding of the inner tube 32, and thus, the material M is less likely to fall out of or be dislodged from the basket-type collecting unit 500. Thus, the material M can be collected securely and removed from the human body by drawing out either the material collecting accessory 100 or the endoscope.

As a further example, the grasping unit 5 of the above embodiments may be replaced with a high-frequency snare unit 600. The high-frequency snare unit 600 is used to excise polyps or the like. In this case, a high-frequency connection plug (not illustrated) is connected to the proximal end of the manipulation wire 33 so that a high-frequency current for treatment can be passed via the manipulation wire 33 to the snare unit 600 from an external high-frequency power supply.

Similar to the above, the snare unit 600 is connected to the manipulation wire 33 via the connecting tube 6. The snare unit 600 is formed, for example, from two stranded stainless steel wires 600a that are joined at a distal end by a front end tip 610 and are formed such that in a neutral state the wires 600a form a loop, as shown in FIG. 17.

Figure 18:
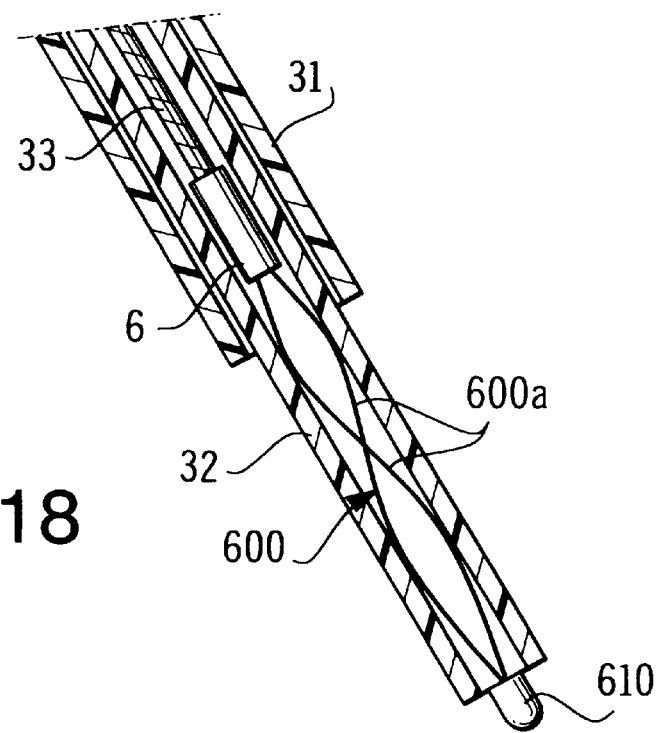
FIG. 18 is an enlarged sectional side view of the alternative material collecting accessory of FIG. 17 in a closed state.

If the snare unit 600 is provided to the material collecting accessory 100 of the first embodiment as an example, as shown in FIGS. 5 and 18, when the grasping area 24 is brought closer to the support 12 (that is, by closing the hand), the distal end of the inner tube 32 protrudes from the distal end of the outer tube 31 and closes the snare unit 600.

Figure 17:
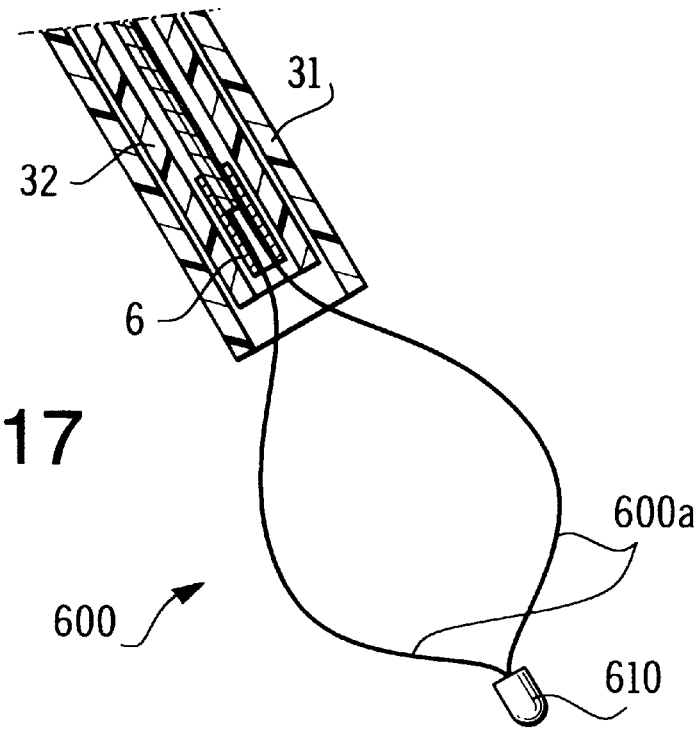
FIG. 17 is an enlarged sectional side view of another alternative material collecting accessory.

Also, as shown in FIGS. 4 and 17, when the grasping area 24 is moved away from the support 12 (that is, by opening the hand), the distal end of the inner tube 32 moves inside the distal end of the outer tube 31 allowing the snare unit 600 to open resiliently.

When inserting the material collecting accessory 100 through the instrument insertion channel of an endoscope the palm of the operator's hand is closed so that the insertion part 30 passes through the instrument insertion channel with the snare unit 600 closed.

Figure 19:
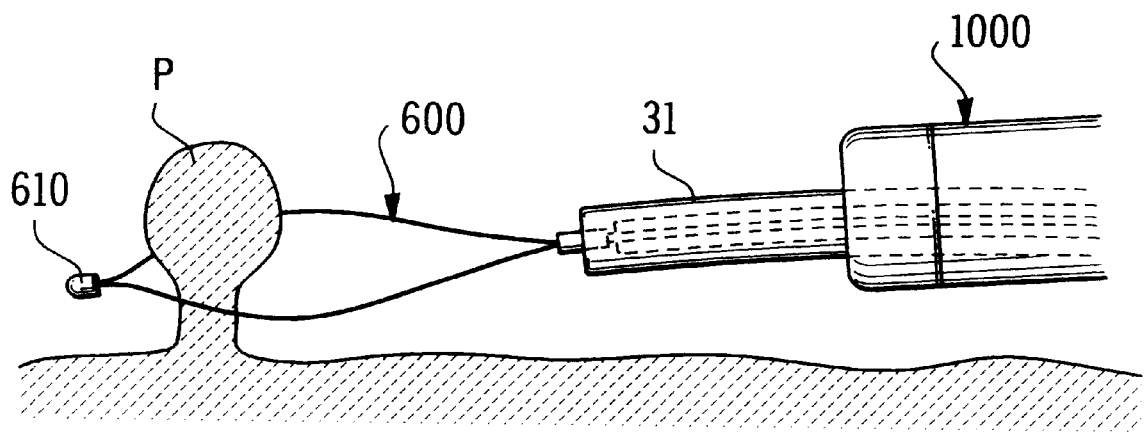
FIG. 19 is a side view illustrating the operation of the material collecting accessory of FIG. 17.
Figure 20:
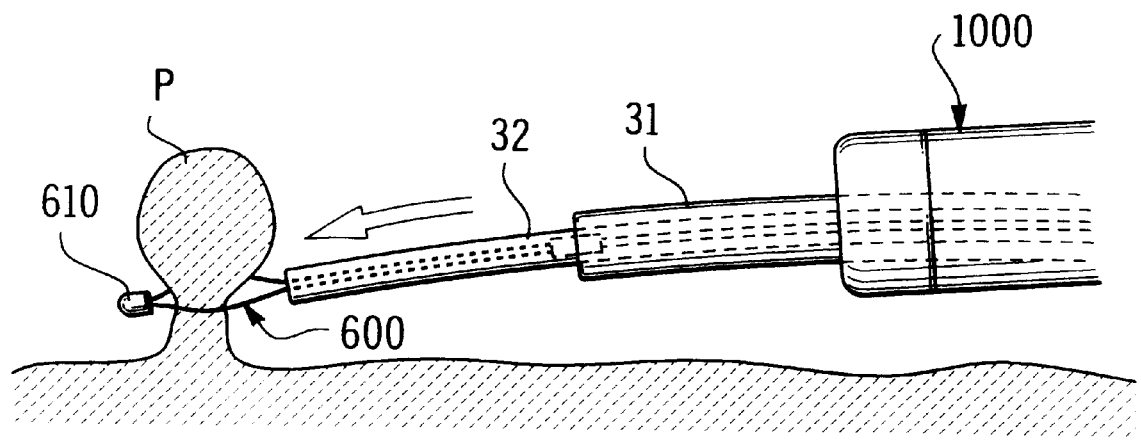
FIG. 20 is a side view illustrating the operation of the material collecting accessory of FIG. 17 in a closed state.

Once inside a human body, the snare unit 600 is opened by opening the hand (as shown in FIG. 4) and the outer tube 31 is positioned so that a polyp P is positioned inside the opened snare unit 600 (as shown in FIG. 19). At this point, the outer tube 31 is fixed in position by a forceps plug, clamp, or the like (not shown) provided at a proximal end of the endoscope so that an operator can then accurately operate the first and second manipulation parts 10, 20. The operator then closes the hand (as shown in FIG. 5) to slide the inner tube 32 over the snare unit 600 and close the snare unit 600 (as shown in FIG. 20). In this operation, since the outer tube 31 is fixed in the axial direction, the snare unit 600 remains fixed in the axial direction while being closed by the sliding of the inner tube 32, and thus, the polyp P is less likely to slide free of the snare unit 600. Thus, the polyp P can be accurately excised.

As indicated above, the present invention can also be applied to other operative instruments and further, is not limited to medical instruments but may also be applied to industrial instruments.

Also as indicated above, the position of the operator's hand may be varied according the situation or preference of the operator.

Although the structure and operation of a treatment accessory for an endoscope is described herein with respect to preferred embodiments and examples, many other modifications and changes can be made without departing from the spirit and scope of the invention.

The present disclosure relates to subject matters contained in Japanese Patent Applications Nos. HEI 08-148950, filed on Jun. 11, 1996, HEI 08-161217, filed on Jun. 21, 1996, HEI 08-162793, filed on Jun. 24, 1996, and HEI 08-162794, filed on Jun. 24, 1996, which are expressly incorporated herein by reference in their entireties.

What is claimed is:

1. A treatment accessory for use with an endoscope, said treatment accessory having a proximal end nearest the user and a distal end remote from a user, and said treatment accessory comprising:

a treatment unit having a closed state and an open state, and biased to be in the open state;

an inner tube;

an outer tube coaxially positioned with respect to said inner tube and extending beyond a distal end of said inner tube when said treatment unit is in said open state;

a manipulation wire slidably positioned within said inner tube, a distal end of said manipulation wire attached to said treatment unit, and said distal end of said manipulation wire being substantially at said distal end of said inner tube when said treatment unit is in said open state;

a first manipulation part including a first grasping portion by which said treatment accessory is held, said first manipulation part connected to a proximal end of said manipulation wire;

a second manipulation part including a second grasping portion by which said treatment accessory is held, said second manipulation part connected to a proximal end of said inner tube;

a main body connected to a proximal end of said outer tube;

a single connecting rod that connects said first manipulation part and said main body, said connecting rod being spaced from and parallel to an axis of said manipulation wire, exposing a proximal end of said inner tube and said manipulation wire for cleaning access in a circumferential range only excepting said connecting rod, said connecting rod and said manipulation wire being positioned on either side of an axial center line of said first grasping portion and said second grasping portion, said manipulation wire being surrounded by a rigid member for preventing buckling of said manipulation wire when said first grasping portion is operated along said axial center line;

a fixing device that engages said first manipulation part and at least one of said connecting rod and said manipulating wire, said fixing device enabling attachment and detachment of said at least one of said connecting rod and said manipulation wire to and from said first manipulation part;

wherein said second manipulation part is slidable along said connecting rod toward said main body, and wherein said first manipulation part, said main body, said manipulation wire, and said outer tube are interconnected so that when said first and second grasping portions are separated, said inner tube extends relative to said manipulating wire and said outer tube so that said inner tube closes said treatment accessory.

2. The treatment accessory according to claim 1, wherein said connecting rod is detachable from one of said first manipulation part and said second manipulation part.

3. The treatment accessory according to claim 1, wherein said manipulation wire is detachable from said first manipulation part.

4. The treatment accessory according to claim 1, wherein said treatment unit is formed to resiliently open.

5. The treatment accessory according to claim 4, wherein said treatment unit is closed when said inner tube slides to cover a portion of said treatment unit adjacent to said distal end of said manipulation wire.

6. The treatment accessory according to claim 1, said instrument unit comprising a grasping collecting unit.

7. The treatment accessory according to claim 1, said instrument unit comprising a basket-type collecting unit, said basket-type collecting unit including a plurality of flexible wires connected to each other at both ends.

8. The treatment accessory according to claim 1, said instrument unit comprising a snare unit, said snare unit comprising at least one flexible wire formed into a loop.

9. The treatment accessory according to claim 8, said snare unit comprising a high-frequency snare unit.

10. The treatment accessory according to claim 1, said fixing device comprising a screw extending transverse to said axis of said manipulating wire.

11. The treatment accessory according to claim 1, said fixing device detachably attaching said first manipulation part and said connecting rod.

12. The treatment accessory according to claim 1, said fixing device detachably attaching said first manipulation part and said manipulating wire.

13. The treatment accessory according to claim 1, said fixing device comprising screw members detachably attaching said at least one of said connecting rod and said manipulating wire to said first manipulation part.

14. The treatment accessory according to claim 1, said connecting rod having a threaded portion that is threadedly engaged with a hole provided on said main body.

15. The treatment accessory according to claim 1, said second manipulation part including a hole extending through said second manipulation part, said hole being substantially coaxial with the axis of said manipulation wire, said manipulation wire extending through said hole, at least a portion of said manipulation wire covered by said rigid member passing through said second manipulation part when said second manipulation part slides along said connecting rod.

* * * * *